United States Patent [19]
Jansen

[11] Patent Number: 5,549,669
[45] Date of Patent: * Aug. 27, 1996

[54] INTRAOCULAR LENS HAVING HAPTICS WITH NON-SYMMETRICAL CROSS-SECTION

[75] Inventor: Peter Jansen, Uithuizen, Netherlands

[73] Assignee: Pharmacia AB, Stockholm, Sweden

[ * ] Notice: The term of this patent shall not extend beyond the expiration date of Pat. No. 5,376,115.

[21] Appl. No.: 309,988

[22] Filed: Sep. 20, 1994

Related U.S. Application Data

[63] Continuation-in-part of Ser. No. 99,333, Aug. 2, 1993, Pat. No. 5,376,115.
[51] Int. Cl.⁶ ..................................................... A61F 2/16
[52] U.S. Cl. ................................................................ 623/6
[58] Field of Search ...................................... 623/6

[56] References Cited

U.S. PATENT DOCUMENTS

| | | | |
|---|---|---|---|
| 4,244,060 | 1/1981 | Hoffer | 623/6 |
| 4,573,998 | 3/1986 | Mazzocco | 623/6 |
| 4,648,878 | 3/1987 | Kelman | 623/6 |
| 4,702,244 | 10/1987 | Mazzocco | 623/6 X |
| 4,710,195 | 12/1987 | Giovinazzo | 623/6 |
| 4,863,465 | 9/1989 | Kelman | 623/6 |
| 4,871,362 | 10/1989 | Nurmamedov et al. | 623/6 |
| 4,990,159 | 2/1991 | Kraff | 623/6 |
| 5,071,432 | 12/1991 | Baikoff | 623/6 |

*Primary Examiner*—Mary Beth Jones
*Attorney, Agent, or Firm*—Dinsmore & Shohl

[57] ABSTRACT

An intraocular lens includes an optical lens body and haptics extending outwardly from the optical lens body. Each of the haptics is defined by a plane and includes at least a portion having a cross-section which is non-symmetrical with respect to the plane of the haptic.

5 Claims, 3 Drawing Sheets

5,549,669

INTRAOCULAR LENS HAVING HAPTICS WITH NON-SYMMETRICAL CROSS-SECTION

RELATED APPLICATION

This application is a continuation-in-part of U.S. application Ser. No. 08/099,333 filed Aug. 2, 1993, now U.S. Pat. No. 5,376,145.

FIELD OF THE INVENTION

The present invention is related to the field of ophthalmology and more specifically to new intraocular lenses (IOL's) which have been found to considerably facilitate and improve the result of IOL implantation.

BACKGROUND OF THE INVENTION

A most common age related observation is that visual acuity is reduced when the lens of the eye becomes cloudy, thereby making the vision blurred. This opacification of the lens is called cataract and is caused by molecular rearrangement of the lens components with increased light-scattering. Some cataracts furthermore develop a yellow-brown color due to pigment deposition which also contributes to a further reduction of vision.

The most frequent cataracts occur in elderly people; however, the lens of the eye might also be affected in this manner due to diabetes or numerous types of injuries.

The only treatment of cataracts which is available is to remove the cloudy lens through surgery. Once the lens has been removed a new artificial lens is required so that the eye can focus clearly. There are three methods of restoring vision after cataract surgery: by cataract spectacles, by contact lenses or by implantation of intraocular lenses.

An intraocular lens implant is prepared from a biocompatible material, for instance polymethylmethacrylate (PMMA) or silicone, and is placed inside the eye by the surgeon in direct connection with the cataract removal.

Cataract surgery has changed dramatically over the past twenty years, principally as a result of the introduction of the operating microscope, introduction of viscoelastic substances such as Healon®, better instrumentation, improved surgical techniques and refinement of the intraocular lens implants as such. The state of the art methods are constantly being developed and improved.

Heretofore most intraocular lens implantations have involved first making an incision 1 in the cornea as indicated in FIG. 1 and then filling the anterior segment of the eye with a viscoelastic material. After extraction of the natural lens, an IOL is then inserted through the incision, FIG. 2, manipulated past the iris, FIG. 3 and then seated closely adjacent the posterior wall of the lens capsule, FIG. 4. The IOL shown in FIGS. 2-4 has the two haptics attached to the lens at an angle α which is referred to as the degree of angularion, which is shown in FIG. 5. This angle is often about 10 degrees.

A surgical method gaining in popularity is the phacoemulsification technique, which utilizes ultrasonic vibrations to fragment the lens nucleus, thus allowing removal of the lens material through an incision that is approximately 3 mm long. The benefits of a small incision are faster visual rehabilitation, faster healing and less astigmatism than with conventional large incisions. A hollow titanium needle with a diameter of about 1 mm is activated to vibrate by a magnetostrictive ultrasonic mechanism. The mechanical vibrations transform the lens into an emulsion, hence the name phacoemulsification.

As the phacoeemulsification technique has been refined, the construction of the incision has been developed to allow sealing of the wound without the need for sutures. This incision technique is referred to in the art as "self sealing incisions".

Such a self sealing incision is based on the valve being constructed through an internal lip of corneal tissue that is pressed towards the outer part of the wound by the internal pressure in the eye as shown in FIG. 6. The valve can be made either entirely in the cornea, shown by reference numeral 3, "clear cornea incision", or partly in the sclera, shown by reference numeral 2, "scleral tunnel incision". The operation must be very accurately performed. For a cornoscleral tunnel the scleral incision is made 1–2.5 mm peripheral to limbus, that is the grey line separating the clear cornea from the white sclera. Using a knife with a rounded tip, a tunnel/valve is fashioned, about one-half scleral depth and about 3 mm wide and 2 mm long. This is followed by the incision into the anterior chamber. Using a knife with a pointed tip the tunnel/valve is extended into the clear cornea another 1–2 mm with exactly the same careful precise motion. Following this procedure a very accurate valve construction is prepared. After removal of the opacified lens the incision is extended to the size required for the intraocular lens to be implanted, the anterior segment of the eye is filled with a viscoelastic material and the lens is implanted. Minimizing the size of the lens and manipulation of the lens during implantation are accordingly of great importance in order to allow the use of very small incisions, which are often referred to as tunnel incisions. The tunnel or small incision technique is described for instance in *J. Cataract Refract. Surg.* 16(5), 1990, p. 567–77, by Menapace et al. and in *Ophthalmology* (US), 100(2), 1993 p. 159–63, by Ormerod et al.

A conventional incision 1 as shown in FIG. 1, which is closer to the limbus, and which enters the anterior chamber straight does not have the advantages discussed above. Tunnel incision offers, for reasons mentioned above, great advantages, but it is of crucial importance that lenses suitable for the procedure are available. In this connection considerable efforts have been made to develop a foldable lens which can be deformed during the insertion step but which after insertion in the eye returns to the predetermined size. This concept is disclosed in U.S. Pat. Nos. 4,702,244 and 4,573,998.

Once the lens is inserted, it must be carefully manipulated in order to avoid damaging portions of the eye and to ensure proper placement. For example, during insertion there is a risk of the leading haptic or loop touching the inside of the cornea, see FIG. 7. The cornea contains a layer of endothelial cells which are extremely sensitive to mechanical damage. The function of the endothelial cell layer is to allow the aqueous component into the cornea and to pump out excess fluid so that transparency is maintained. The pump is located in the cell membranes of the endothelium. The cells are hexagonal in shape and seem to be fitted together much as tiles on a floor. The hexagonal configuration minimizes mechanical stress between units. Mechanical damage to the endothelial cells results in the mechanism described above being disturbed and can further cause cell death and if significant cell death occurs the cornea becomes edematous and opaque, and corneal transplantation is required. Thus, it is helpful for the surgeon to be able to see the haptics during insertion of the lens.

Additionally, it is essential that the haptics can be seen when the surgeon maneuvers the lens through the iris in order to secure that the lens is properly placed in the bag.

For those reasons, there are lenses having colored haptics which allow better visual observation of the haptics during insertion and placement of the lens. The colored haptics are easy to achieve when making a three piece lens but are much more difficult to provide when the lens is produced in one piece from a lens blank.

Accordingly, a need exists in the art for intraocular lenses which include haptics that are easily seen during implantation and which are conveniently produced.

SUMMARY OF THE INVENTION

As a result, I have now developed a new concept for an intraocular lens in which the haptics are more easily observed during insertion and placement of the lens, which lens may be easily manufactured and overcomes disadvantages of prior art lenses.

Specifically, I have recognized that prior art one-piece lenses having haptics with substantially rectangular or quadratic cross-sections are difficult to see during surgery owing to their optical characteristics, i.e, their reflection and refraction characteristics. I have discovered that a haptic with a non-symmetrical cross-section with respect to the plane of the haptic has different optical characteristics which make the haptic easy to see and to follow during insertion into and placement in the capsule. This characteristic accordingly makes the implantation much more convenient and safe. Accordingly, the intraocular lenses of the present invention include an optical lens body and haptics extending outwardly from the optical lens. The haptics are each defined by a plane and at least a portion of each of the haptics has a cross-section which is non-symmetrical with respect to the plane of the haptic. The haptics thereby exhibit reflection and refraction characteristics which allow the haptics to be easily seen during insertion and placement, thereby facilitating implantation of the intraocular lenses in the eye.

These and additional advantages provided by the intraocular lenses of the present invention will be more fully apparent in view of the following detailed description.

BRIEF DESCRIPTION OF THE DRAWINGS

The following detailed description of the present invention will be more fully understood in view of the drawing in which.

DETAILED DESCRIPTION

Figure 1:
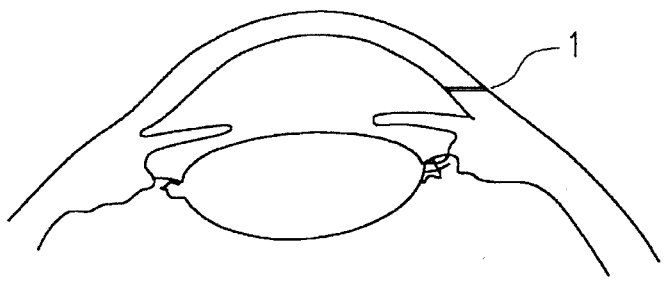
FIG. 1 shows making an incision in the cornea.
Figure 2:
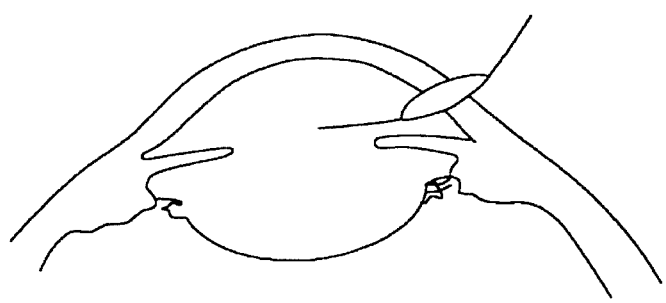
FIG. 2 shows inserting a conventional IOL through the incision.
Figure 3:
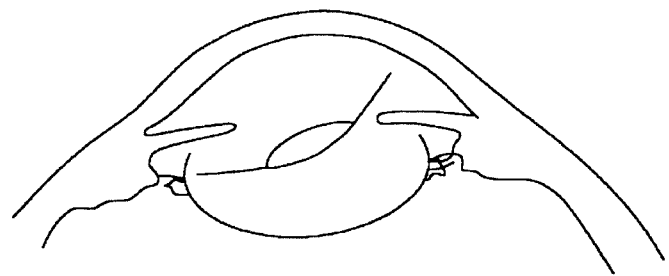
FIG. 3 shows manipulating a conventional IOL past the iris.
Figure 4:
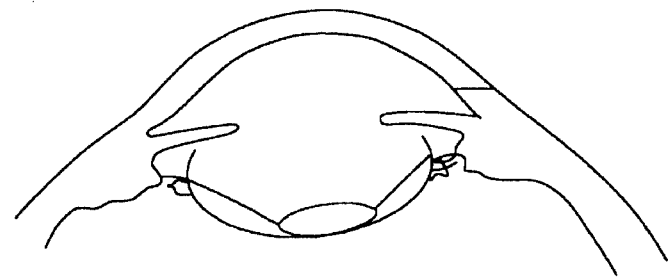
FIG. 4 shows a conventional IOL seated in the lens capsule.
Figure 5:
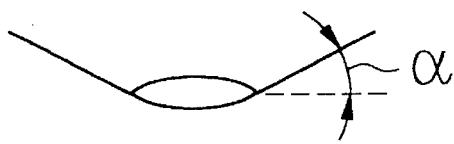
FIG. 5 shows a conventional IOL in which haptics are angulated with respect to an optical portion.
Figure 6:
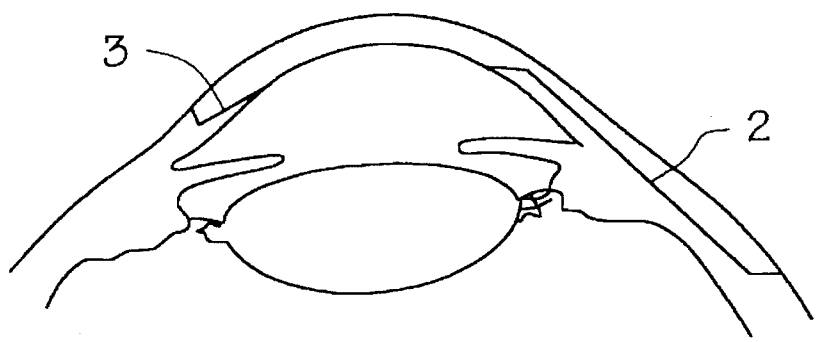
FIG. 6 shows a self-sealing incision.
Figure 7:
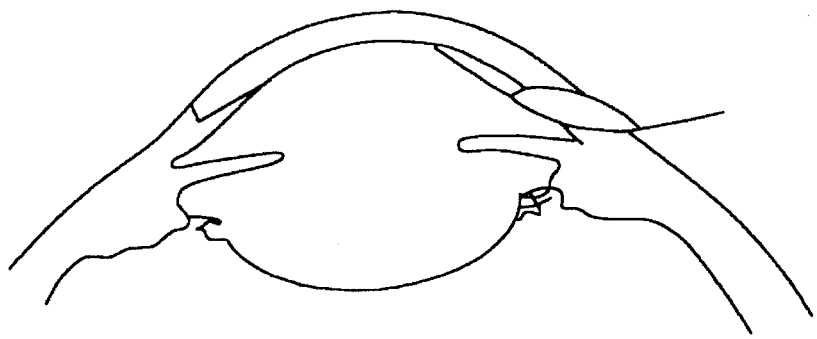
FIG. 7 shows insertion of a conventional IOL through an incision.

The intraocular lenses of the present invention comprise an optical lens body and haptics extending outwardly from the optical lens body. Each of the haptics is defined by a plane. The optical lens body is also defined by a plane which may or may not be coplaner with the planes defining the haptics. In a preferred embodiment, each haptic is angulated with respect to the optical lens body plane, for example at an angle of up to about 10°, as shown in FIG. 5.

Figure 8:
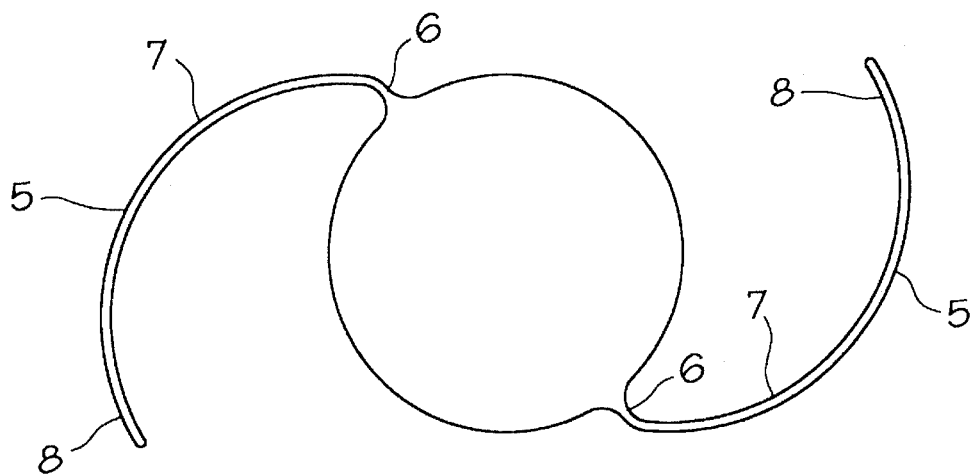
FIG. 8 shows an IOL according to the invention.
Figure 9:
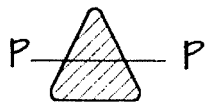
FIG. 9 shows a cross-section of a haptic according to a first embodiment.
Figure 10:
FIG. 10 shows a cross-section of a haptic according to a second embodiment.

In accordance with an important feature of the invention, at least a portion of each haptic has a cross-section which is non-symmetrical with respect to the plane of the haptic. A lens according to the invention is shown in FIG. 8. The lens 10 includes an optical lens body 4 and haptics 5. Each haptic includes a connecting portion 6, which connects with an optical lens body, an intermediate portion 7, and an end portion 8.

Figure 11:
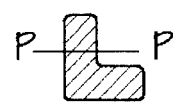
FIG. 11 shows a cross-section of a haptic according to a third embodiment.
Figure 12:
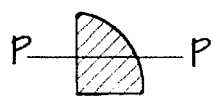
FIG. 12 shows a cross-section of a haptic according to a fourth embodiment.

At least a portion of each haptic has a non-symmetrical cross-section with respect to the plane P—P defining the haptic as exemplified by FIGS. 9–12. For example, in FIG. 9, the non-symmetrical cross-section haptic portion has an isosceles triangular cross-section while in FIG. 10, the non-symmetrical cross-section haptic portion has an equilateral triangular portion. In FIG. 11, the non-symmetrical cross-section haptic portion has an L-shaped cross-section and in FIG. 12, the non-symmetrical cross-section haptic portion has a quarter circle shaped cross-section. In each of these embodiments, the entire haptic or only a portion thereof has the described non-symmetrical cross-section. If only a portion of the haptic has the non-symmetrical cross-section as described above, this portion may be the connecting portion 6, the intermediate section 7 or the end portion 8, or a combination thereof. As a result, the haptic exhibits optical characteristics, i.e., refraction and reflection properties, which allow the haptic to be easily seen during implantation of the lens. Any portions of the haptic which are not non-symmetrical, i.e. are symmetrical, may be, for example, rectangular.

A lens accordingly to the invention has been found to make the insertion through a tunnel/valve more safe and easy to carry out as compared with a conventional IOL. Specifically, intraocular lenses with haptics having a non-symmetrical cross-section as described above are much easier to see during implantation. As discussed above, it is essential that the haptics can be seen when the surgeon maneuvers the lens through the iris in order to secure that the lens is properly placed in the bag.

The lens according to the invention may be made from any conventional lens materials and are easily manufactured in one piece from a lens blank. Other manufacturing methods known in the art may also be employed.

The specific embodiments described above are provided to illustrate the present invention and are not intended to limit the scope of the invention. Other embodiments within the claimed invention will be apparent to those skilled in the art.

I claim:

1. An intraocular lens including an optical lens body and haptics extending outwardly from the optical lens body, each haptic being defined by a plane, the improvement comprising each haptic having a cross-section along its entire length which is non-symmetrical with respect to the plane of said haptic.

2. An intraocular lens according to claim 1, wherein said haptics have a triangular cross-section.

3. An intraocular lens according to claim 1, wherein said haptics have an L-shaped cross-section.

4. An intraocular lens according to claim 1, wherein said haptics have a quarter circle-shaped cross-section.

5. An intraocular lens according to claim 1, wherein said haptics are angulated with respect to a plane defined by the optical lens body.

* * * * *